United States Patent [19]

Popoff et al.

[11] Patent Number: 4,896,668
[45] Date of Patent: Jan. 30, 1990

[54] PLATE SET FOR OSTEAL FIXATION, EQUIPPED WITH SUTURE STRANDS

[75] Inventors: Georges Popoff, Paris; Georges Schwarz, Goussainville, both of France

[73] Assignee: Peters, Aubervilliers, France

[21] Appl. No.: 36,305

[22] Filed: Apr. 9, 1987

[30] Foreign Application Priority Data

Apr. 10, 1986 [FR] France ................... 86 05146

[51] Int. Cl.⁴ .................. A61B 17/08; A61F 5/04
[52] U.S. Cl. ........................ 606/74; 606/232
[58] Field of Search .......... 128/335, 337, 92 YD, 128/92 YF

[56] References Cited

U.S. PATENT DOCUMENTS

| | | | |
|---|---|---|---|
| 3,648,705 | 3/1972 | Lary | 128/335 |
| 3,730,187 | 5/1973 | Reynolds | 604/178 |
| 3,831,608 | 8/1974 | Kletschka et al. | 128/335 |
| 3,885,570 | 5/1975 | Leveen | 128/335 |
| 3,927,423 | 12/1975 | Swanson | 128/92 YD |
| 4,210,148 | 7/1980 | Stivala | 128/335 |
| 4,512,346 | 4/1985 | Lemole | 128/335 |
| 4,583,541 | 4/1986 | Barry | 128/335 |

FOREIGN PATENT DOCUMENTS

| | | | |
|---|---|---|---|
| 0014823 | 9/1980 | Fed. Rep. of Germany | 128/92 F |
| 0052998 | 6/1982 | Fed. Rep. of Germany | 128/92 F |
| 0065098 | 11/1982 | Fed. Rep. of Germany | 128/335.5 |

OTHER PUBLICATIONS

Engineering in Medicine, vol. 9, No. 3, July 1980, pp. 127–130, London, GB; J. A. Bradley et al.: "Carbon Fibre Reinforced Plastics for Load-Bearing Implants".

Primary Examiner—William H. Grieb
Assistant Examiner—Gary Jackson
Attorney, Agent, or Firm—Scully, Scott, Murphy & Presser

[57] ABSTRACT

A sternum plate set for securing a patient's ribcage following surgery and for protecting internal organs during subsequent surgical procedures. The plate set is constructed of biocompatible material intended to be implanted into a patient's body during a surgical procedure behind the sternum and to remain in contact with or as a substitute for the sternum following surgery. The plate set is slightly convex in shape on a side facing the sternum, and is provided with at least one transverse channel having a suture strand and passing therethrough. The suture strand has free ends which are equipped with curved needles and are passed through the sternum and joined together to secure the plate behind the sternum so that the plate permanently remains inside the patient's body between the sternum and internal organs.

8 Claims, 2 Drawing Sheets

PLATE SET FOR OSTEAL FIXATION, EQUIPPED WITH SUTURE STRANDS

FIELD OF THE INVENTION

The present invention belongs to the field of instruments and articles for medical and/or surgical use. Its subject is an osteal fixation plate equipped with suture strands and capable of being left permanently in place in contact with or as a substitute for a bony part of the human or animal body. The invention finds an especially advantageous application in the field of sternotomy which will be used hereinafter to illustrate, by way of example, the problem which underlies the present invention.

In many surgical operations in which the surgeon has to operate in the thoracic cavity, for example during operations on the lungs, the heart or the major arteries, he is obliged to open the thorax in order to gain access to the organs. Generally, this opening is performed by means of a vertical sternotomy. After this operation, the surgeon necessarily has to close the sternotomy again. For this purpose, he employs individual suture strands which are generally crimped on curved needles. For each closure of the sternum he employs between 3 and 6 sutures, depending on the volume of the thorax or the length of the sternum.

Currently, in France, cardiovascular surgeons each year perform approximately 30,000 operations requiring access by means of vertical sternotomy. In each operation of this type, the surgeons employ sutures of the abovementioned type to close the thorax, once the operation is finished. The sutures, which pass around or through the sternum like a hoop, are used to hold securely the two sides of the bone, so that natural consolidation, which requires several weeks, can take place.

One of the complications encountered at this stage is the separation of the two sides of the sternum which may lead to pseudoarthrosis which may, or may not, be infected.

It sometimes also happens, especially in older subjects, that the suture strands, which consist of thick, robust sutures, give rise to severe damage to the bones, especially to the sternum, and this may be irreversible because of the brittle nature of these tissues.

The use of individual suture strands, without cross-connections, can thus be accompanied by serious mechanical disadvantages.

Furthermore, all the patients who have had the benefit of an operation involving vertical sternotomy are liable, in the months or years which follow, to the risk of a repeated operation using the same access route. Now, after the first operation, adhesions are formed between the posterior face of the sternum and the neighboring organs. These organs may be the pleurae or the lungs, the pericardium, if it may have been approached, the large vessels of the mediastinum, particularly the innominate venous trunk of the aorta, or the anterior parts of the heart itself (right auricle or right ventricle). All these organs can become closely adherent to the sternum.

It will be understood that, in such conditions, the reopening of the sternum by means of the oscillating saw in the course of the repeat operation or operations involves a rare but unpredictable danger of breaking through into the organ, with a risk of cataclysmic hemorrhage.

This phenomenon does not occur during the initial operation, because the heart and the major vessels which lead therefrom are enclosed in the pericardium (a fibrous membrane), which can easily be moved aside.

PRIOR ART

EP-A-No. 0,014,823 (Howmedica) describes a small bar of short length (maximum 80 mm) capable of being fastened onto the ribs in order to hold these in the event of fracture or damage. For this purpose, the small bar is equipped with pointed crampons which are pushed into the ribs. Its function is therefore only that of a splint. The characteristics of a small bar of this kind make it unsuitable for use as an osteal fixation plate, especially for the sternum after sternotomy. Furthermore, the said known small bar does not comprise suture strands. Thus, EP-A-No. 0,014,823 does not make it possible to solve the technical problem consisting in producing a structure which simultaneously provides the osteal fixation and a correct placing of the suture strands, so as to avoid disintegration of the stressed bones (such as the sternum) and to protect the underlying organs, especially in the case of a new surgical operation.

U.S. Pat. No. 3,730,187 (Reynolds) illustrates a catheter for urethral drainage, which is equipped beforehand with a suture strand to enable it to be secured. It is quite clear that a device of this kind cannot solve the technical problem just mentioned.

BRIEF SUMMARY OF THE INVENTION

A subject of the present invention is a plate set for osteal fixation, chiefly of the sternum after sternotomy, which provides a solution to a problem of this kind. This plate serves as an implant and not a prosthesis. In addition, it simplifies the surgeon's work, by virtue of the fact that it is equipped with separately held suture strands onto which the needles are crimped, the whole being packaged in a sterile pack.

Another subject of the present invention is a plate set which may be left in place permanently, in contact with or substituting for a bone, for example the sternum, in order to get rid of the disadvantages found in the prior art with the use of individual suture strands.

The invention relates, therefore, to a plate set which comprises a plate of biocompatible material, intended to be put in place during a surgical operation and to remain in contact with or as a substitute for a bone, the said plate carrying at least one suture strand whose free ends are intended to be linked together to hold the plate resting against the bone.

The plate set according to the invention fulfills a number of functions. First of all, when put in place, the plate acts as a protector and stiffens the assembly with the bone. In addition, it prevents the suture strands from damaging the bone or from producing irreversible incidents thereon particularly owing to its fragility. These advantages are particularly noticeable in the case of a sternotomy. The plate set strengthens the robustness of the union of the two sides of the sternum. The presence of the plate prevents the suture strands from sawing the posterior face of the sternum owing to excessive clamping, or because of a possible fragility of the bone. In addition, when placed in position, the plate fulfills a protective function in the respect of the underlying organs. In the illustrative example of the sternotomy, the plate of the invention, by being inserted between the sternum and the underlying organs, eliminates the danger in the event of a repeat operation because, while sawing through the bone, the surgeon can initially encounter only the separation plate. The plate set fulfills still another function, since it carries the suture strands. This enables the surgeon to have at his disposal a number of sutures which are well located and easy to handle, in contrast to the prior art, in which he was obliged to handle individual sutures. In addition to this function of supporting the suture strands, the plate set according to the invention thus provides the surgeon with greater ease of handling.

Within the meaning of the present description, the expression "suture strands" has the same meaning as that given to this expression in the current art. The invention offers the greatest benefit when the suture strands are thick sutures of high mechanical strength, of stainless steel or of another material, such as polyester.

The material of which the plate according to the invention is made is not critical, but it is essential that it should be biocompatible, that is to say that it should be chosen from materials which have been demonstrated to be harmless, nontoxic and nonirritant; thus, the plate may be made either of metal such as stainless steel or tantalum, or of plastic such as polyester, polypropylene, polyethylene, polyvinylidene fluoride, polytetrafluoroethylene, polyhexafluoroethylene and other similar materials. These last three materials are preferred, since they are known and have been used as biomaterials for some time.

Other plastics present a risk of deterioration in the long term and metal plates may be inconvenient by causing unwanted resonance during NMR examinations.

The shape of the plate of the invention is not critical and it will have to be adapted to the local needs to take into account the characteristics of the bones with which it is to interact. In the case where the plate is employed resting against the sternum, it is of overall elongate rectangular shape.

It is advantageous for the plate to have a degree of flexibility as a whole, although mechanical strength remains a major factor. Thus, in the case of sternotomy, the plate should be designed to match closely the curvature of the thorax. Still for the same reason, the above-mentioned plastics are particularly highly suitable.

The other constituent of the plate set according to the invention consists of at least one suture strand. In order to secure the suture strands to the plate and to facilitate the positioning of the sutures, in a first embodiment the sutures pass through corresponding holes provided in the plate. The holes are provided such that the sutures can slide so that they can be adjusted and can be centered automatically when the surgeon ties his knot in the case of polyester sutures or twists the two strands of wire in the case of stainless steel sutures.

In an alternative embodiment, however, the sutures may also be firmly fastened to the plate. In this case, the suture strands may be fastened by welding or by adhesion, or, alternatively, they may also be threaded through holes or chicanes in the plate so that they are held therein.

It goes without saying that the number of suture strands depends on the nature of the surgical operation to be performed. The separation between the suture strands is calculated so that the holding in position and the securing to the bone are optimal.

In the case of a sternotomy, the plate made of biomaterials is generally provided with 6 suture strands. This number corresponds to the maximum quantity which is usually employed by the surgeons.

In the case of a shorter or smaller sternum, for example in the event of an operation on a woman or on a child, the surgeon may section the plate in at least one place which is provided, to shorten it and at the same time to remove one or two sutures which he no longer requires.

To this end, the plate according to the invention may be provided with one or more small incisions which enable the surgeon to cut off the excessive length easily.

For practical reasons, the needles which are crimped in pairs and fastened to the same suture are folded back, linked together and held in position by a plastic tube or by a foam and the sutures which are folded back are separated from each other by plastic sheets or sheaths so as not to mix up the various suture strands and to make the plate easier to position during the operation.

BRIEF DESCRIPTION OF THE DRAWINGS

The invention will now be illustrated, without being limited in any way, by the description which follows, which relates to a plate set capable of being used in sternotomy and which refers to the attached drawings, in which.

DETAILED DESCRIPTION OF PREFERRED EMBODIMENTS

Figure 1:
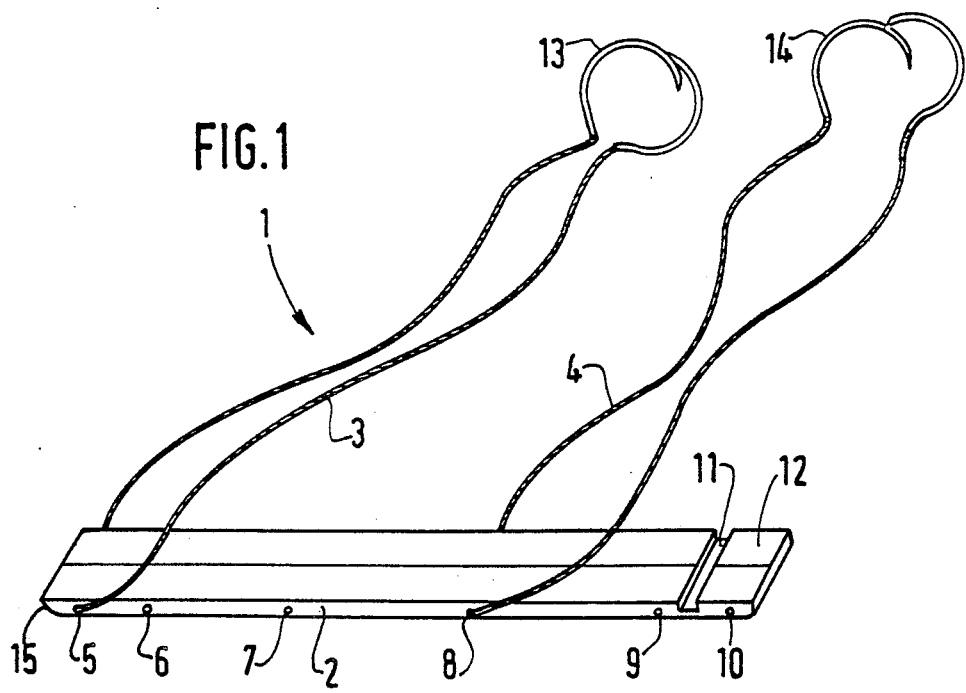
FIG. 1 shows, in perspective, the plate set with two suture strands.

As shown in FIG. 1, the plate set according to the invention is denoted by the general reference (1). It comprises a plate (2) of elongate rectangular shape. To give an example, this plate may be 20 cm in length and 2 cm in width. To give it sufficient flexibility, its thickness is 4 mm. The plate (2) is equipped with a number of suture strands, only two of which, the strands (3, 4), are shown. These strands are made of stainless steel and may comprise curved needles such as (13, 14) at their ends. In the example chosen, the suture strands slide freely in transverse openings in the plate (2). These openings carry references (5, 6, 7, 8, 9 and 10) and they are six in number in the example chosen. To simplify the illustration in the drawing, only two suture strands (3, 4), which pass, respectively, through the openings (5, 8) are shown. The plate normally comprises six suture strands.

At one of its ends, the plate (2) comprises a breakage initiator (11) enabling the surgeon, where appropriate, to separate the end portion (12), in order to shorten the length of the plate.

At the other end, shown at (15), there is a chamfered portion so as to adapt to surgical requirements as much as possible.

It goes without saying that the above example is merely an illustration and the invention is not limited in any manner to the form of rectangular plates. Similarly, the plate profiles may vary. In addition, the plate may be given a curvature or may be reinforced in some places, should this be found necessary.

Figure 2:
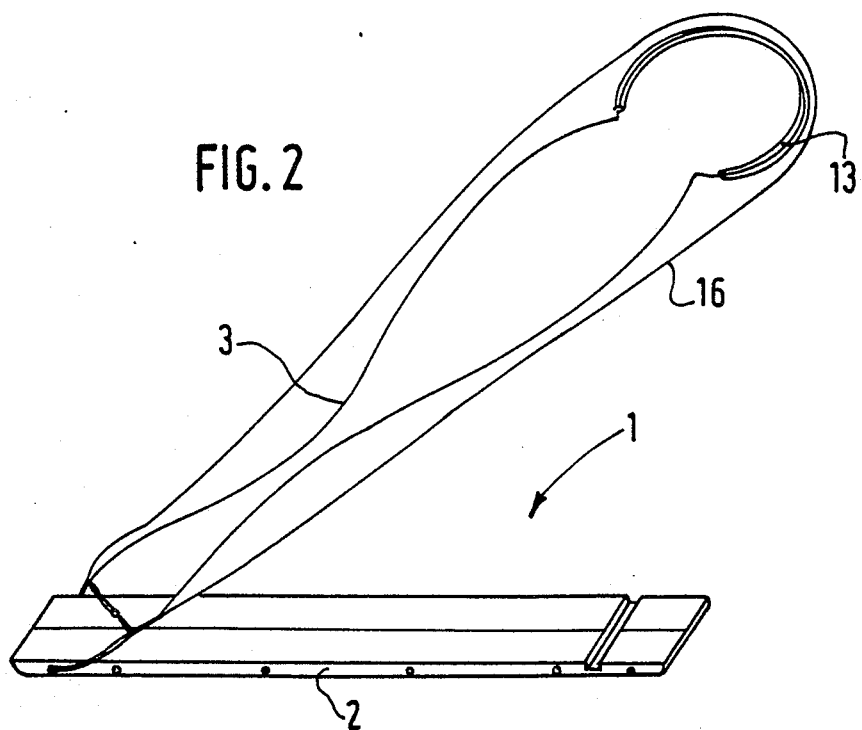
FIG. 2 is a view similar to FIG. 1, showing a suture strand in a plastic sheath.

FIG. 2 is a view similar to FIG. 1, in which only one suture strand (3) is shown. Otherwise, the plate (2) is identical and there is therefore no need to repeat the whole description in its respect. The objective of FIG. 2 is to illustrate the embodiment according to which the suture strand (3) is surrounded by a transparent plastic sheath (16) which protects the needles (13). In practice, all the sets of suture strands are equipped with a sheath of this kind. To ensure sterility of the whole, provision is also made for introducing the plate set, with its suture strands surrounded respectively by a protective sheath, into a plastic enclosure whose edges have been sealed. The surgical sterilization requirements are thus met.

Figure 3:
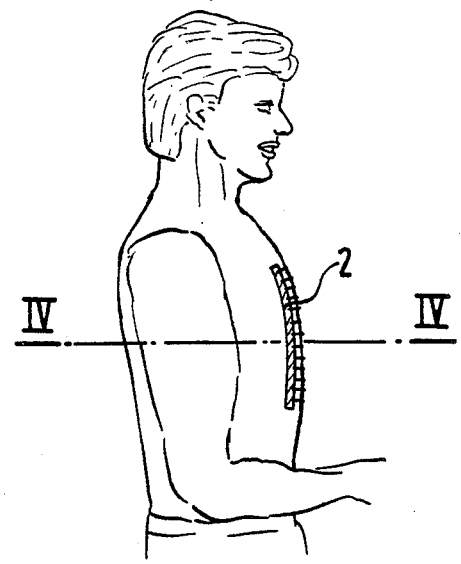
FIG. 3 is a diagram illustrating the positioning of the plate set.

FIG. 3 illustrates diagrammatically the permanent mounting of the plate (2) on the anterior portion of the thorax of a human subject who has undergone a sternotomy.

Figure 4:
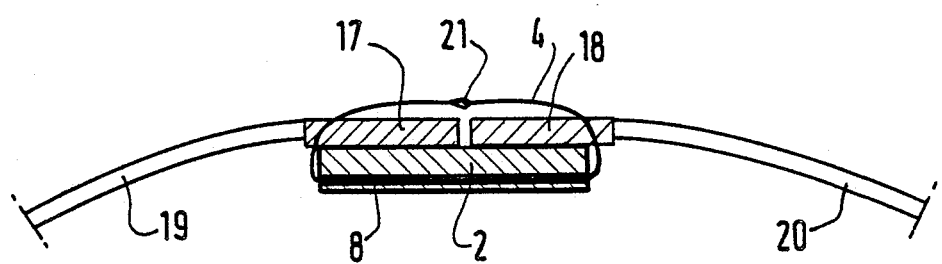
FIG. 4 is a horizontal cross-section taken in the plane IV—IV of FIG. 3.

FIG. 4 illustrates, in greater detail, the positioning of the plate set (2). It can be seen that the plate (2) rests on the two portions (17, 18) of the sternum, which have been sectioned during the operation. The ribs attached to the sternum in this region are shown at (19, 20). A suture strand such as (4) passes through the opening (8) in the plate (2). The free ends of the suture are secured as shown at (21). It will be noted that to ensure optimum strength, the portion of the plate (2) which rests against the sternum (17, 18) is of greater thickness than that of the opposite portion.

The advantages of putting the plate (2) in place have been clearly demonstrated in the introduction to this specification. There is therefore no need in repeating them now in the description of a specific example. Once again, for the purpose of description the latter has been chosen from the field of sternotomy. It goes without saying, however, that the invention can be applied to other fields of surgery.

Furthermore, the invention has been shown in the drawings in a diagrammatic manner, the sole objective being to illustrate it. The specialist is capable of introducing alternative versions therein without departing thereby from its scope. Thus, a single sectionable incision (11) has been shown. It goes without saying that a number of these incisions may be provided in order to adapt the plate to body dimensions.

What is claimed is:

1. A sternum plate set for securing a patient's ribcage following surgery and for protecting internal organs during subsequent surgical procedures, comprising a plate of biocompatible material intended to be implanted into a patient's body during a surgical operation behind the sternum and to remain in contact with or as a substitute for the sternum, said plate having a slightly convex shape on a side facing said sternum, said plate being provided with at least one transverse channel having a suture strand passing therethrough, said suture strand having free ends intended to be passed through the sternum and joined together to secure the plate behind the sternum and resting against the sternum such that the plate permanently remains inside the patient's body between the sternum and internal organs.

2. The plate set as set forth in claim 1, wherein the plate consists of a biocompatible material having the properties of harmlessness, nontoxicity and nonirritability, particularly of stainless steel or tantalum, or alternatively of polyester, polypropylene, polyethylene, polyvinylidene fluoride, polytetrafluoroethylene or polyhexafluoroethylene.

3. The plate set as set forth in either of claims 1 or 2, wherein said slightly convex shape of the plate adapts said plate for contact with the internal surface of said sternum.

4. The plate set as set forth in claim 3, wherein the plate has at least one transverse notch such that said plate is sectionable by breaking said plate at said notch.

5. The plate set as set forth in claim 1, wherein the suture strands are thick sutures of high mechanical strength and made of stainless steel or polyester.

6. The plate set as set forth in claim 1 wherein the suture strands are firmly and nonremovably secured through the plate in said transverse channels.

7. The plate set as set forth in claim 6, wherein the suture strands carry curved needles.

8. A method of securing the sternum of the patient following surgery involving splitting of said sternum, comprising placing a biocompatible plate set behind said sternum between the patient's internal organs and said sternum, said plate set having a slightly convex shape on a side facing said sternum, said plate being provided with at least one transverse channel having a suture strand passing therethrough, said suture strand having free ends provided with curved needles; passing said sutures and needles through said sternum and securing said sutures to close and secure said sternum, such that said plate set remains permanently within said patient's body to reinforce said sternum and to protect said internal organs during subsequent surgical operations.

* * * * *